United States Patent [19]

Brittain et al.

[11] Patent Number: 4,544,662
[45] Date of Patent: Oct. 1, 1985

[54] 1'-SUBSTITUTED-SPIRO[OXAZOLIDINE-5-3'-INDOLINE]-2,2', 4-TRIONE DERIVATIVES

[75] Inventors: David R. Brittain, Macclesfield; Robin Wood, Stockport, both of United Kingdom

[73] Assignee: Imperial Chemical Industries, England

[21] Appl. No.: 492,246

[22] Filed: May 6, 1983

[30] Foreign Application Priority Data

May 7, 1982 [GB] United Kingdom ................. 8213206

[51] Int. Cl.$^4$ ................. C07D 498/10; C07D 263/44; A61K 31/42
[52] U.S. Cl. .................... 514/374; 548/216; 549/486
[58] Field of Search .......................... 548/216; 424/272

[56] References Cited

U.S. PATENT DOCUMENTS 4,200,642  4/1980  Schnur ................................. 548/216
4,226,875  10/1980 Schnur ................................. 548/216

FOREIGN PATENT DOCUMENTS 028906   5/1981  European Pat. Off. ............ 548/309
79675    5/1983  European Pat. Off. ............ 548/216
2028318  3/1980  United Kingdom ................. 548/216

OTHER PUBLICATIONS

Clark-Lewis et al., J. Chem. Soc., 1965, 5551–5556.

Primary Examiner—Donald G. Daus
Assistant Examiner—S. A. Gibson
Attorney, Agent, or Firm—Cushman, Darby & Cushman

[57] ABSTRACT

The invention provides novel spiro[oxazolidine-5,3'-indoline]-2,2',4-triones of formula I bearing substituted benzyl or cinnamyl on the indoline nitrogen, together with salts and non-toxic, biodegradable precursors thereof. The compounds are potent inhibitors of the enzyme aldose reductase and are useful in treating or preventing certain diabetic complications. The invention also provides pharmaceutical compositions containing, and processes for the manufacture of, the compounds of formula I and their salts and derivatives.

5 Claims, No Drawings

1'-SUBSTITUTED-SPIRO[OXAZOLIDINE-5-3'-INDOLINE]-2,2', 4-TRIONE DERIVATIVES

This invention concerns novel indoline derivatives and, more particularly, 1'-substituted-spiro[oxazolidine-5,3'-indoline]-2,2',4-trione derivatives which are potent inhibitors of the enzyme aldose reductase. The invention also concerns pharmaceutical compositions of, and processes for the manufacture of, such compounds.

The enzyme aldose reductase is responsible in man and other warm-blooded animals for the catalytic conversion of aldoses, for example glucose and galactose, to the corresponding alditols, for example sorbitol and galactitol respectively. Alditols penetrate cell membranes poorly and, once formed, tend to be removed only by further metabolism. As a consequence, alditols tend to accumulate within cells where they are formed, for example in the lens, peripheral nerve tissue and kidney, causing a rise in internal osmotic pressure which may in turn be sufficient to destroy or impair the function of the cells themselves. In addition, raised alditol levels may result in abnormal levels of their metabolites which may themselves impair or damage cellular function. However, the enzyme aldose reductase has a relatively low substrate affinity, that is, it is only effective in the presence of relatively large concentrations of aldose. Such large concentrations of aldose are present in the clinical conditions of diabetes (excessive glucose) and galactosemia (excessive galactose). As a consequence, inhibitors of the enzyme aldose reductase are useful in the reduction or prevention of the development of those complications of protracted diabetes or galactosemia which may be due in part to the accumulation of sorbitol or galactitol respectively. Such complications are, for example, macular oedema, cataract, retinopathy, nephropathy or impaired neural conduction.

It is known that certain spiro-oxazolidinediones obtained from 4H-2,3-dihydrobenzopyran-4-one and related heterocyclic ketones are inhibitors of the enzyme aldose reductase (UK patent application publication No. 2028318A), for example at concentrations of approximately $10^{-6}M$. We have now discovered a series of oxazolidinediones (I) obtained from 1-substituted-indoline-2,3-diones and which are potent inhibitors of the enzyme aldose reductase, for example at concentrations of approximately $10^{-8}M$.

According to the invention there is provided a 1'-substituted-spiro[oxazolidine-5,3'-indoline]-2,2',4-trione of the formula I:

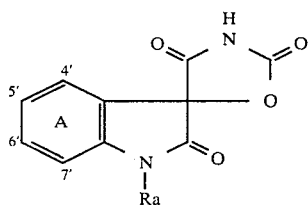

wherein Ra is cinnamyl bearing one or two halogeno nuclear substituents, or Ra is benzyl bearing one or two substituents independently selected from halogeno and trifluoromethyl, located at position 2, 3, 4 or 5; and benzene ring A bears one or two substituents independently selected from halogeno, trifluoromethyl and (1-4C)alkyl, located at position 5', 6' or 7'; or a salt with a base affording a pharmaceutically acceptable cation; or a non-toxic, biodegradable precursor thereof.

The compounds of formula I are derivatives of spiro[oxazolidine-5,3'-indoline]-2,2',4-trione which will be numbered throughout this specification as shown in formula Ia

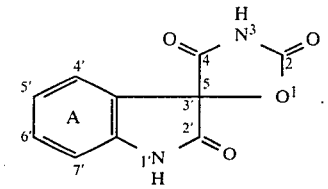

In this specification Ra, Rb et cetera are used to depict generic radicals and have no other meaning.

The compounds of formula I all possess at least one asymmetric carbon atom (namely the spiro carbon atom at position 5 of the oxazolidine ring) and therefore exist, and may be isolated, in one or more racemic and optically-active forms. This invention includes compounds of formula I in racemic form or in any optically-active form which possess aldose reductase inhibitory properties, it being well known in the art how to prepare optically-active forms by resolution of the racemic form, or by synthesis from optically-active starting materials, and how to determine the aldose reductase inhibitory properties by the standard tests described hereinbelow.

A particular value for Ra when it is cinnamyl bearing one or two halogeno substituents is, for example, 4-chloro-, 4-bromo- or 3,4-dichlorocinnamyl.

Particular values for substituents which may be present on benzene ring A or as part of Ra when it is substituted benzyl are, by way of example
for halogeno: fluoro, chloro, bromo or iodo; and
for (1-4C)alkyl: methyl or ethyl.

The term non-toxic, biodegradable precursor includes derivatives of the compounds of formula I defined above in which the imino hydrogen atom in the oxazolidine ring is replaced by a biodegradable protecting group known in the art, which group is not inherently toxic and which is capable of removal in vivo (for example by enzymic hydrolysis) to liberate the compound of formula I in sufficient quantity to inhibit the enzyme aldose reductase and without giving rise to pharmacologically unacceptable by-products. Examples of suitable groups for inclusion in biodegradable precursors of compounds of formula I include alkoxycarbonyl, aralkoxycarbonyl, alkoxyoxalyl and 1-(alkanoyloxy)alkyl groups, such as ethoxycarbonyl, t-butyloxycarbonyl, benzyloxycarbonyl, ethoxyoxalyl, methoxyoxalyl and pivaloyloxymethyl groups. In general, the biodegradable precursors are not themselves inhibitors of the enzyme aldose reductase, but are active in vivo by virtue of removal of the biodegradable protecting radical. It will be apparent, therefore, that by suitable choice of biodegradable protecting groups (for example based on their generally known rates of enzymic degradation) it is possible to produce biodegradable precursors of compounds of formula I whose bioabsorption and distribution properties differ from those of the compounds of formula I.

Specific values for benzene ring A of particular interest are, for example, when it bears a fluoro, chloro, bromo, methyl, or trifluoromethyl substituent located in the 7'-position, optionally together with another substituent as defined above in position 5' or 6'.

Specific values for Ra of particular interest are, for example, when it is halogenocinnamyl (especially 4-chlorocinnamyl), halogeno- or (trifluoromethyl)benzyl [especially 4-chlorobenzyl,4-bromobenzyl, (3-trifluoromethyl)benzyl or (4-trifluoromethyl)benzyl], or dihalogenobenzyl (especially 2,4-dichlorobenzyl, 4-chloro-2-fluorobenzyl, 4-bromo-2-fluorobenzyl, 2-fluoro-4-iodobenzyl, 3,4-dichlorobenzyl, 3-bromo-4-chlorobenzyl or 4-bromo-3-chlorobenzyl).

In general, it is preferred that benzene ring A bears at least one halogeno substituent.

A preferred group of novel compounds of the invention comprises compounds of the formula II

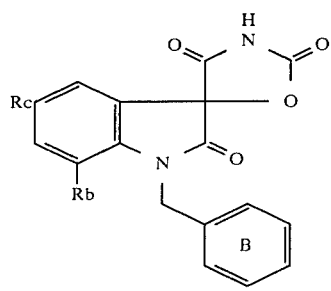

wherein Rb is halogeno, (1-4C)alkyl or trifluoromethyl; Rc is hydrogen or halogeno; and benzene ring B is selected from 4-bromophenyl, 3,4-dichlorophenyl, 3,4-dibromophenyl, 3-bromo-4-chlorophenyl, 4-bromo-3-chlorophenyl, 4-bromo-2-fluorophenyl and 2-fluoro-4-iodophenyl; or a salt with a base affording a pharmaceutically acceptable cation; or a non-toxic, biodegradable precursor thereof.

Illustrative compounds of the invention, by way of example are:

1'-(3,4-dichlorobenzyl)-5'-chloro-7'-methylspiro[oxazolidine-5,3'-indoline]-2,2',4-trione;

1'-(4-bromo-2-fluorobenzyl)-7'-methylspiro[oxazolidine-5,3'-indoline]-2,2',4-trione; and 1'-(3,4-dichlorobenzyl)-7'-fluorospiro[oxazolidine-5,3'-indoline]-2,2',4-trione; or a pharmaceutically acceptable salt; or a non-toxic, biodegradable precursor thereof.

A preferred non-toxic, biodegradable precursor is, for example, a pivaloyloxymethyl derivative of a compound of formula I.

Particular salts of compounds of formula I with bases affording a pharmaceutically acceptable cation are, for example, alkali metal or alkaline earth metal salts (such as sodium, potassium, calcium or magnesium salts), aluminium or ammonium salts, or salts with organic bases (such as triethanolamine).

The novel compounds of formula I may be obtained by any process known in the art for the manufacture of structurally analogous compounds. Such processes are provided as a further feature of the invention and are illustrated by the following presently preferred procedure which is characterised by cyclising a compound of the formula III

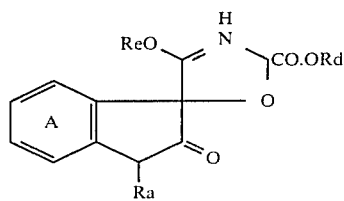

wherein Ra and benzene ring A have the meanings given above, Rd is (1-6C)alkyl, or optionally substituted phenyl or benzyl, and Re is hydrogen or (1-6C)alkyl.

A particular value for Rd or Re when it is (1-6C)alkyl is, for example, methyl, ethyl or butyl.

A particular value for Rd when it is optionally substituted phenyl or benzyl is, for example, phenyl, 4-methylphenyl, 4-chlorophenyl, benzyl, 4-methylbenzyl or 4-methoxybenzyl.

It will be appreciated that when Re is hydrogen the compound of formula III may exist in the predominant tautomeric form IIIa

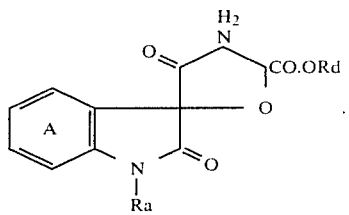

The process is normally carried out in the presence of a base catalyst, for example in the presence of an alkali metal carbonate, acetate, formate or hydride, such as potassium carbonate, sodium acetate, sodium formate or sodium hydride, and preferably under essentially non-aqueous conditions, for example in a suitable solvent or diluent such as toluene, xylene, 1,2-dimethoxyethane, 1,4-dioxane or N,N-dimethylformamide. The process is usually carried out at elevated temperature, conveniently at or near the boiling point of the reaction mixture, but may also be performed at a temperature in the range, for example, 20°–150° C.

In some cases, when Re is (1-6C)alkyl an intermediate of the formula IV

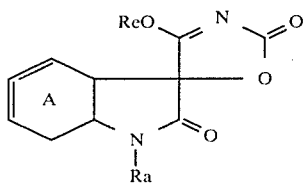

may initially be isolated from the above process, but is generally readily hydrolysed by mild acidic hydrolysis.

The starting materials of formula III may be obtained by reaction of the appropriate 1-substituted isatin of the formula V

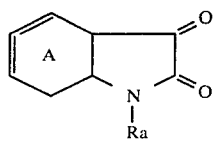

with an alkali metal cyanide (such as potassium cyanide), an alkali metal hydroxide (such as potassium hydroxide), and a chloroformate of the formula RdO.CO.Cl wherein Rd has the meaning defined above, at a temperature in the range, for example, 0° to 40° C., to give the corresponding nitrile of the formula VI

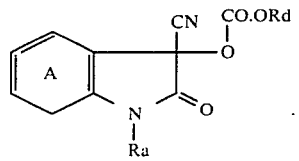

This nitrile may then readily be converted to the corresponding carbamoyl derivative of formula IIIa (formula III, Re=H) or imidate derivative of formula III [Re=(-1-6C)alkyl] by treatment, respectively, with aqueous hydrogen chloride, or with anhydrous hydrogen chloride and the appropriate (1-6C)alkanol, conveniently at a temperature of, for example, 0° to 30° C. The imidate derivative of formula III [Re=(1-6C)alkyl] is normally isolated as its hydrochloride salt and may be used in this form in the process of the invention provided that the free base form is first liberated in situ by reaction with a molecular equivalent of base.

Many of the isatins of formula V are known compounds, but they are all obtainable by conventional alkylation of the appropriate substituted isatin in a solvent such as N,N-dimethylformamide using the appropriate cinnamyl or benzyl bromide or chloride.

The non-toxic, biodegradable precursors of the compounds of formula I may be obtained by known acylation or alkylation procedures already used for the introduction of the necessary biodegradable protecting radicals. Examples of suitable acylating or alkylating reagents for incorporating a range of such protecting radicals are, for example, alkoxycarbonyl, aralkoxycarbonyl, alkoxyoxalyl and 1-(alkanoyloxy)alkyl halides, such as ethoxycarbonyl, t-butyloxycarbonyl, benzyloxycarbonyl, ethoxyoxalyl, methoxyoxalyl and pivaloyloxymethyl chloride.

The reaction may be performed under conventional N-acylation/alkylation conditions, for example in the presence of a base such as potassium carbonate or using the lithium, sodium or potassium salt of the compound of formula I, and in a suitable solvent or diluent, for example 1,2-dimethoxyethane, dibutyl ether or diethyl ether, at a temperature in the range, for example 10°-80° C.

An alternative process which may be used for the production of compounds of formula I involves reacting a 1'-unsubstituted compound of the formula Ia with a halide of the formula Ra.X wherein X is chloro, bromo or iodo in the presence of a suitable base, for example an alkali metal hydride, hydroxide or carbonate, preferably in a suitable solvent or diluent, for example N,N-dimethylformamide or dimethyl sulphoxide, and at a temperature in the range, for example, 15° to 100° C. The starting materials of formula Ia may be obtained by conventional procedures of organic chemistry well known in the art.

The pharmaceutically acceptable salts of compounds of formula I may be obtained by conventional procedures, for example by reaction with the appropriate base affording a pharmaceutically acceptable cation.

When an optically active form of a compound of formula I is required, a racemic form of the said compound may be reacted with an optically-active form of a suitable organic base, for example brucine, coniine, 2-pipecoline, amphetamine or an N,N,N-trialkyl-(1-phenyl-ethyl)ammonium hydroxide such as N,N,N-trimethyl-(1-phenylethyl)ammonium hydroxide, followed by conventional separation of the diastereoisomeric mixture of salts or complexes thus obtained, for example by fractional crystallisation from a suitable solvent, for example a (1-4C)alkanol, whereafter the optically-active form of the said compound may be liberated by treatment with acid using a conventional procedure, for example using an aqueous mineral acid, such as dilute hydrochloric acid.

The property of inhibiting the enzyme aldose reductase may be demonstrated in the following standard laboratory test. Thus, rats are made diabetic (as evidenced by severe glucosuria being present) by dosing with streptozotocin. The animals are then dosed daily with the test compound for 5 days. The animals are then killed and the eye lenses and sciatic nerves are removed. After a standard work-up procedure the residual sorbitol levels in each tissue are determined by gas liquid chromatography after conversion to the poly-trimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats.

A modified test may also be used in which the streptozotocin induced diabetic rats are dosed daily with test compound for two days. The animals are killed 2-4 hours after the final dose. The sciatic nerves are then removed and assessed for residual sorbitol levels as described above.

In general the compounds of formula I produce significant inhibition of the enzyme aldose reductase (as measured by the effects on residual sorbitol levels) in either of the above tests at an oral dose of 50 mg./kg. or much less without any signs of overt toxicity or other untoward effects at the active dose or several multiples thereof.

The property of inhibiting the enzyme aldose reductase may also be demonstrated in vitro. Thus, purified aldose reductase is isolated in known manner from bovine lenses. The percentage inhibition of this enzyme's ability in vitro to reduce aldoses to polyhydric alcohols, and particularly to reduce glucose to sorbitol, caused by a test compound is then determined using standard spectrophotometric methods. In this test the compounds of formula I in general show significant inhibition of the enzyme aldose reductase at a concentration in the region of $10^{-8}M$. For example, the preferred compounds of Example 6 and 7 have an $IC_{50}$ (concentration necessary to produce 50% inhibition of enzymic activity) of $2 \times 10^{-8}M$ and $2.5 \times 10^{-8}M$, respectively.

Compounds of formula I possessing potent inhibitory properties in this in vitro test and yet not particularly active by oral administration in the above in vivo tests may nevertheless be applied in an in vivo therapeutic or prophylactic situation, for example by topical administration direct to the tissue or organ in which inhibition of the enzyme is required, for example by topical administration to the eye. However, the compounds of formula I will primarily be administered systemically (generally by mouth) to a warm-blooded animal to produce an inhibitory effect on the enzyme aldose reductase, for example at a daily dose of 0.5 to 25 mg./kg. In man it is envisaged that a total daily dose in the range 25 to 750 mg. per man will be administered, given if necessary, in divided doses.

The compounds of formula I will normally be administered to warm-blooded animals in the form of special pharmaceutical formulations. The invention therefore also provides a pharmaceutical composition comprising a compound of formula I, or one of its pharmaceutically-acceptable salts, or one of its non-toxic, biodegradable precursors, in admixture or conjunction with a pharmaceutically-acceptable diluent or carrier.

The compositions may be in a form suitable for oral administration, for example in the form of a tablet, capsule, granule, dispersible powder, syrup, elixir, emulsion, suspension or gel; for parenteral administration, for example in the form of a sterile injectable aqueous suspension or solution, or oily solution or suspension; for rectal administration, for example in the form of a suppository; or for topical administration to the eye, for example in the form of an ointment, gel or sterile solution buffered at an opthalmically acceptable pH, for example in the range pH 7.0–7.6.

Topical formulations may be administered to the eye of an animal, for example man or dogs, requiring treatment for diabetic cataracts or retinopathy in a conventional manner, for example using a drop or eyewash topical formulation.

The compositions may also contain one or more other agents which are known to have a useful effect in the treatment of diabetes or galactosemia, for example a hypoglycaemic agent such as tolbutamide, chlorpropamide, or glybenclamide.

The invention will now be illustrated by the following non-limiting Examples in which, unless otherwise stated:

(i) all evaporations were carried out by rotary evaporation in vacuo;
(ii) all operations were carried out at room temperature, that is in the range 18°–26° C.;
(iii) petroleum ether (b.p. 60–80) is referred to as "petrol 60–80"; and
(iv) all compounds of formula I were characterised by satisfactory elemental microanalysis and spectroscopic examination.

EXAMPLE 1

Potassium carbonate (6.0 g.) was added to a solution of 3-benzyloxycarbonyloxy-1-(3,4-dichlorobenzyl)-7-fluoro-2-oxoindoline-3-carboxamide (2.0 g.) in toluene (100 ml.). The mixture was stirred and heated under reflux for 1 hour. The toluene was removed by evaporation and the residue partitioned between ether (100 ml.) and water (100 ml.). The aqueous phase was adjusted to pH 5 with 2M hydrochloric acid. The ether phase was then separated, washed with water, brine and then dried (MgSO$_4$) and evaporated to give 1'-(3,4-dichlorobenzyl)-7'-fluorospiro[oxazolidine-5,3'-indoline]-2,2',4-trione, as a solid, m.p. 140°–142° C. (recrystallised from ethyl acetate/petrol 60–80).

The starting material was obtained as follows:

A solution of potassium cyanide (1.0 g.) in water (4 ml.) was added to a stirred solution of 1-(3,4-dichlorobenzyl)-7-fluoroindoline-2,3-dione (5.0 g.) in dichloromethane. Two drops of tricaprylmethylammonium chloride (Aliquat 336, available from Fluka AG, Switzerland) were added to the mixture, and then successive portions (1 ml.) of a solution of benzyl chloroformate (3.94 g.) in dichloromethane (17 ml.) and of a 2M sodium hydroxide solution (7.7 ml.) diluted with water to a volume of 20 ml., were added during 30 minutes. The reaction mixture was then diluted with water (100 ml.) and dichloromethane (100 ml.). The dichloromethane phase was separated, washed with water and then with brine and dried (MgSO$_4$). Evaporation of the dichloromethane gave 3-benzyloxycarbonyloxy-1-(3,4-dichlorobenzyl)-3-cyano-7-fluoroindoline-2-one (Y) as a solid, m.p. 101°–102° C. (recrystallised from methanol).

A solution of Y (2.3 g.) in dioxan (50 ml.) was cooled to 0°–5° C. Hydrochloric acid (11M, 25 ml.) was added and the solution stirred at 0°–5° C. for 30 minutes during saturation with hydrogen chloride. After a further 30 minutes at 0°–5° C. the mixture was allowed to warm up to ambient temperature, and was then poured into iced water (100 ml.). The precipitate which formed was collected, thoroughly washed with water (until the washings were pH 6–7) and dried in vacuo (P$_4$O$_{10}$) to give 3-benzyloxycarbonyloxy-1-(3,4-dichlorobenzyl)-7-fluoro-2-oxoindoline-3-carboxamide (Z) as solid, which was used without further purification.

1-(3,4-Dichlorobenzyl)-7-fluoroindoline-2,3-dione was obtained as a solid, m.p. 147°–148° C. (recrystallised from EtOH/petrol 60–80) by reaction of 3,4-dichlorobenzyl chloride with 7-fluoroisatin in N,N-dimethylformamide at 80°–85° C. using an analogous procedure to that of Schaefer [*Archiv.der Pharmazie (Weinheim)*, 1970, 303, 183–191].

EXAMPLES 2–7

Using a similar procedure to that described in Example 1 the following compounds of formula II were obtained starting from the corresponding ester of formula VI but using sodium hydride in place of aqueous sodium hydroxide and 1, 2-dimethoxyethane in place of toluene, with intermediate formation of the amides of formula IIIa:

| Example | Rb | Rc | Benzene ring B | m.p. (°C.) |
|---|---|---|---|---|
| 2 | CF$_3$ | H | 4-Br—phenyl | 106–108 |
| 3 | Cl | H | 3-CF$_3$—phenyl | 148–150 |
| 4 | Cl | H | 2-F—4-Br—phenyl | 85–87 |
| 5 | H | Cl | 3-CF$_3$—phenyl | 195–196 |
| 6 | CH$_3$ | H | 2-F—4-Br—phenyl | 75–76 |
| 7 | CH$_3$ | Cl | 3,4-Cl$_2$—phenyl | 138–140 |

The starting esters of formula VI were made by an analogous procedure to that described for compound Y in Example 1 starting from the appropriate 1-substituted isatin of formula V and methyl or ethyl chloroformate. The amides of formula IIIa were similarly obtained by analogy with the procedure described for compound Z in Example 1. The melting points for the isolated solids are shown below:

| For Example | Rb | Rc | Benzene ring B | Rd | Esters VI m.p. (°C.) | Amides IIIa m.p. (°C.) |
| --- | --- | --- | --- | --- | --- | --- |
| 2 | CF₃ | H | 4-Br—phenyl | Et | 174–175 | 106–108 |
| 3 | Cl | H | 3-CF₃—phenyl | Et | 168–169 | 148–150 |
| 4 | Cl | H | 2-F—4-Br—phenyl | Me | 146–148 | 112–114 |
| 5 | H | Cl | 3-CF₃—phenyl | Et | 185–187 | 195–196 |
| 6 | CH₃ | H | 2-F—4-Br—phenyl | Me | 156–157 | 120–121 |
| 7 | CH₃ | Cl | 3,4-Cl₂—phenyl | Me | 166–167 | 117–118 |

The necessary isatins of formula V were similarly obtained as described for 1-(3,4-dichlorobenzyl)-7-fluoroisatin in Example 1 and had the following properties:

| Rb | Rc | Benzene ring B | m.p. (°C.) |
| --- | --- | --- | --- |
| CF₃ | H | 4-Br—phenyl | 121–123 |
| Cl | H | 3-CF₃—phenyl | 137–138 |
| Cl | H | 2-F—4-Br—phenyl | 164–166 |
| H | Cl | 3-CF₃—phenyl | 152–154 |
| CH₃ | H | 2-F—4-Br—phenyl | 154–156 |
| CH₃ | Cl | 3,4-Cl₂—phenyl | 191–194 |

EXAMPLE 8

A mixture of 1'-(3,4-dichlorobenzyl)-7'-fluorospiro[oxazolidine-5,3'-indoline]-2,2',4-trione (50 parts), lactose (27 parts) and maize starch (20 parts), was stirred thoroughly and a paste formed from maize starch (2 parts) and water (40 parts) was added and thoroughly mixed in. The resultant mass was passed through a 16 mesh screen, then dried at 60° C. and passed through a 20 mesh screen. Magnesium stearate (1 part) was added to the granules obtained, and the whole compressed by conventional means into tablets, containing 10, 20, 50 or 100 mg. of active ingredient, suitable for oral administration for therapeutic purposes.

The active ingredient may be replaced by any other compound of formula I or a salt or non-toxic biodegradable precursor thereof.

EXAMPLE 9

(All parts by weight)

A mixture of 1'-(4-bromo-2-fluorobenzyl)-7'-methylspiro[oxazolidine-5,3'-indoline]-2,2',4-trione (50 parts), calcium carbonate (20 parts) and polyethyleneglycol (average molecular weight 4000) (3-parts) was vigorously stirred to obtain a uniform powdered form. This material was then charged into gelatine capsules using a conventional procedure such that each capsule contained 10, 20, 50 or 100 mg. of active ingredient suitable for oral administration for therapeutic purposes.

The active ingredient in the above procedure may be replaced by any other compound of formula I or a salt or non-toxic biodegradable precursor thereof.

What is claimed is:

1. A 1'-substituted-spiro[oxazolidine-5,3'-indoline]-2,2',4-trione of the formula:

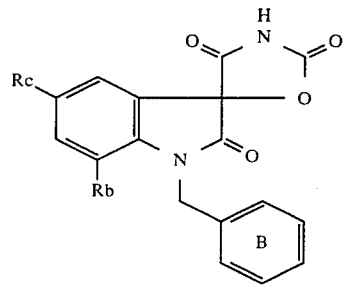

wherein Rb is methyl; Rc is hydrogen or chloro; and benzene ring B is selected from 4-bromophenyl, 3,4-dibromophenyl, 3,4-dichlorophenyl, 3-bromo-4-chlorophenyl, 4-bromo-3-chlorophenyl, 4-bromo-2-fluorophenyl and 2-fluoro-4-iodophenyl.

2. A compound as claimed in claim 1 wherein benzene ring B is 3,4-dichlorophenyl or 4-bromo-2-fluorophenyl.

3. A compound as claimed in claim 1 selected from 1'-(3,4-dichlorobenzyl)-5'-chloro-7'-methylspiro[oxazolidine-5,3'-indoline]-2,2',4-trione, and 1'-(4-bromo-2-fluorobenzyl)-7'-methylspiro[oxazolidine-5,3'-indoline]-2,2',4-trione.

4. A pharmaceutical composition which comprises a compound as defined in claim 1 in admixture or conjunction with a pharmaceutically-acceptable diluent or carrier.

5. A method of inhibiting the enzyme aldose reductase in a warm blooded animal requiring such treatment which comprises administering to said animal an aldose reductase inhibitory amount of a compound as defined in claim 1.

* * * * *